United States Patent [19]
Endico

[11] Patent Number: 5,403,602
[45] Date of Patent: Apr. 4, 1995

[54] OZONE FOOD TREATMENT PROCESS

[76] Inventor: Felix W. Endico, 440 E. 86th St., New York, N.Y. 10028

[21] Appl. No.: 272,245

[22] Filed: Jul. 8, 1994

Related U.S. Application Data

[63] Continuation-in-part of Ser. No. 55,526, Apr. 29, 1993, Pat. No. 5,328,706.

[51] Int. Cl.$^6$ ............... A23L 3/00; G01N 33/00
[52] U.S. Cl. ................... 426/231; 426/335; 426/532
[58] Field of Search ............... 426/231, 335, 532

[56] References Cited
U.S. PATENT DOCUMENTS
4,849,237  7/1989  Hurst .................... 426/532

*Primary Examiner*—George Yeung
*Attorney, Agent, or Firm*—Natter & Natter

[57] ABSTRACT

An ozone food treatment process utilizing ozonized water for releasing oxygen molecules to oxidatively react with food constituents. The oxidative reaction is controlled by the selective introduction of a protein derived enzyme catalyst. The process sterilizes and preserves food products without thermal pasteurization or chemical additives and is particularly adapted for aseptic packaging of fresh foodstuffs.

10 Claims, 1 Drawing Sheet

OZONE FOOD TREATMENT PROCESS

CROSS-REFERENCE TO RELATED APPLICATION

This application is a continuation-in-part of application Ser. No. 08/055,526, filed Apr. 29, 1993, now U.S. Pat. No. 5,328,706.

BACKGROUND OF THE INVENTION

1. Field of the Invention

This invention relates generally to food technology and especially to the application of an oxidatively active natural chemical agent for inhibiting microbial and viral activity in foods.

In particular, the food treatment process of this invention utilizes ozone to sterilize and preserve foods.

2. Background Art

The commercial food processing industry generally relies upon numerous modalities to sterilize and preserve foods. These include heat pasteurization and acidification to disinfect processed foods and chemical additives such as sodium benzoate and potassium sorbate to prevent spoilage and extend the shelf-life of the processed foods.

The sterilization of food implies the use of a process such as thermal energy or bactericides e.g. hydrogen peroxide or chlorine, to destroy microorganisms. The chemical agents employed for sterilization must be rendered inert or the residue thereof must be removed from the food substance in order to meet acceptable government standards.

The chemical additives for preventing spoilage, retarding rancidity and prolonging shelf-life are primarily directed to the reduction of the proliferation of microbes and are generally designated as food preservatives.

A problem with heat pasteurization for sterilizing foods, is that it alters the nutritional profile of the foods. There is also a reductional loss of enzymes, vitamins and minerals within the food. Thermal treatment can also deteriorate the texture, flavor and taste of the food product. Similarly, the use of chemical additives present problems with residues that exceed the proscribed limits set by the governmental agencies. Additionally, chemical additives may impose a health problem to some individuals.

Food treatment with hydrogen peroxide also has shortcomings and can only be used within specific governmental limitations. Furthermore, residual hydrogen peroxide must be removed from the finished food product.

BRIEF SUMMARY OF THE INVENTION

The process of this invention provides a solution to the deficiencies posed by the aforementioned sterilization and food preservation procedures and overcomes the limitations imposed by the use of hydrogen peroxide.

Briefly, the methodology of this invention concerns an ozone food treatment process for sterilization and preservation of foodstuffs. The process involves the delivery of ozone dissolved in water which can be manufactured in situ utilizing electrical discharge synthesis. Ozonized water is also a naturally occurring oxygen enriched substance produced by electrical discharge reactions; its use in food processing should not be inhibited by governmental regulation.

The ozonized water is added to a premix of food constituents. When the ozone molecule decomposes free radical oxygen is released which acts as an oxidizing agent to destroy bacterial growth in the food. The rate of decomposition is controlled during this process and can be accelerated by catalytic intervention.

An advantage of the ozone food treatment process of this invention is that the food mixture can be both sterilized and preserved, depending upon the microbial load and the inoculation of ozonized water, during the process without thermal pasteurization or chemical additives.

Another benefit of the food treatment process utilizing ozone as compared with the hydrogen peroxide, is that it is not necessary to closely monitor the oxidation reaction for the presence of residuary oxidizing agent in the finished food since the ozonized water is a naturally occurring substance.

Another feature of the food treatment process is that the liberated oxygen will destroy bacterial growth without adversely affecting the heat sensitive structural and/or textural quality of the food.

A further aspect of this food treatment process is that fresh food products can be aseptically packaged without heat pasteurization.

In view of the foregoing, it should be apparent that the present invention overcomes many of the problems of the prior art and provides an ozone food treatment process for antimicrobial action upon a wide range of microorganisms and a substantial elimination of the need for chemical food preservatives.

Having thus summarized the invention, it will be seen that it is an object thereof to provide an ozone food treatment process of the general character described herein which is not subject to the aforementioned shortcomings.

Another object of this invention is to provide an ozone food treatment process that is effective for both food sterilization and preservation.

A further object of this invention is to provide an ozone food treatment process wherein the food constituents are treated with ozonized water.

A further object of this invention is to provide an ozone food treatment process wherein an accelerant is utilized for coordinating the attrition rate of the ozone with the corresponding food processing sequence.

Another object of this invention is to provide an ozone food treatment process having the optional capabilities for monitoring the oxidation reaction time.

A still further object of this invention is to provide an ozone food treatment process adapted for automatic batch-feed and continuous-feed food processing operations.

With these ends in view, the invention provides embodiment in the procedures by which the aforementioned objects and certain other objects are hereinafter attained, all as more fully described with reference to the accompanying drawing and the scope of which is more particularly pointed out and indicated in the appended claims.

BRIEF DESCRIPTION OF THE DRAWING

In the accompanying drawing in which is shown an exemplary procedure in accordance with the principles of this invention.

DETAILED DESCRIPTION OF THE INVENTION

Figure 1:
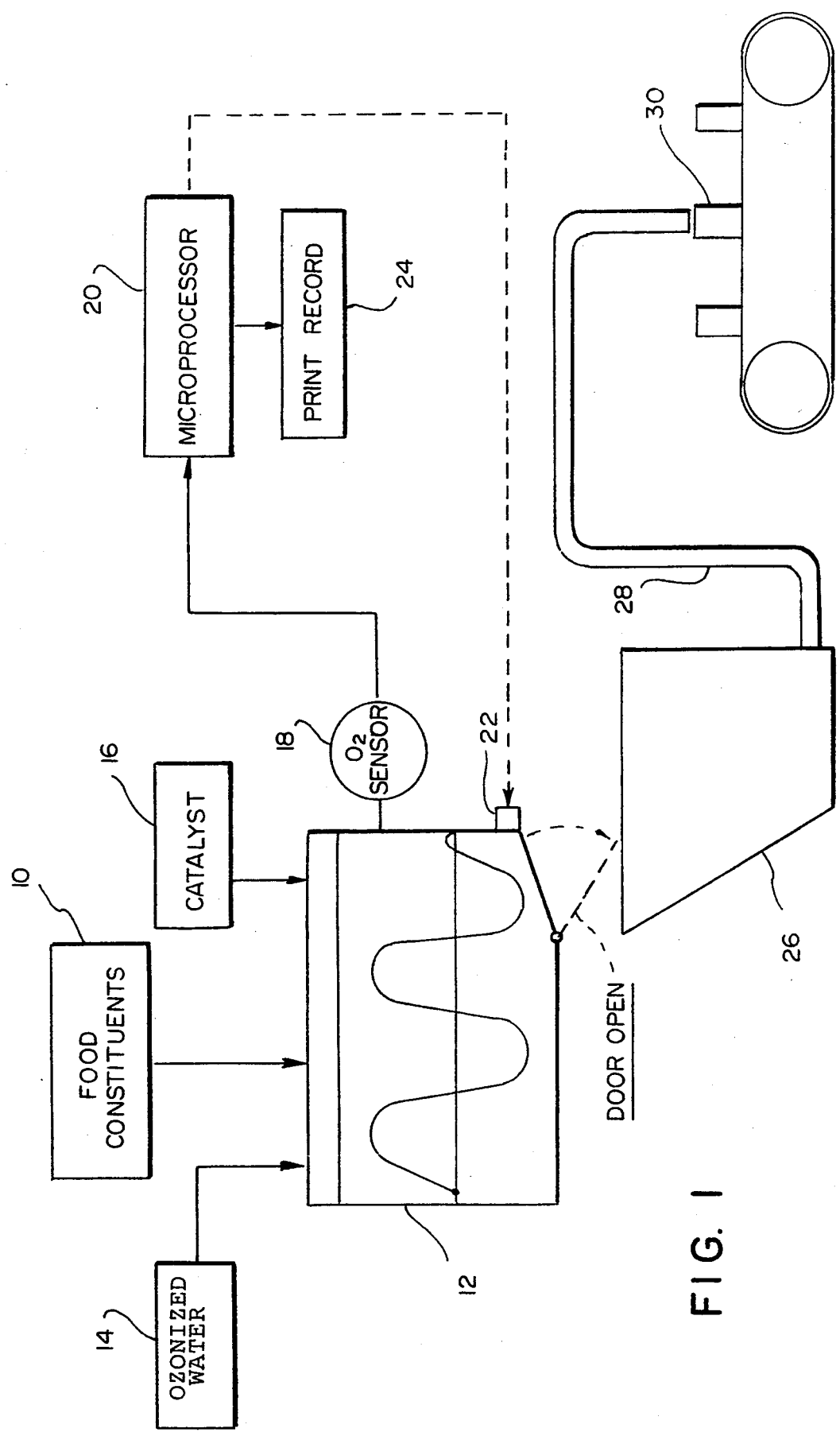
FIG. 1 is a schematic diagram illustrating the ozone food treatment process of this invention as applied to a batch-feed manufacturing operation.

With specific reference now to the drawing, it is stressed that the particulars shown and described herein are for the purpose of illustrative discussion of the process of this invention and are presented in the cause of providing what is believe to be the most useful and readily understood description of the principles and conceptual aspects of the process of this invention. In this regard, no attempt has been made to show the process in more detail than is necessary for a fundamental understanding of the invention however, the description in combination with the drawing should make apparent to those skilled in the art how the process may be applied in practice.

Referring now to FIG. 1, there is shown in schematic diagram, a mixing and packing operation utilizing the ozone food treatment process of this invention. The initial stage of the process involves the formulation of a combination or premix of food constituents 10 including water, condiments and other ingredients as required for the production of selected foodstuffs typically viscous food products, e.g. tuna salad, egg salad, shrimp salad, etc. The process is also adapted for use with semi-viscous flowable food products such as catsup, pickle relish, sauces and salad dressings.

The food constituents 10 are placed within a stainless steel mixing vessel such as a ribbon blender 12. An oxidatively active compound namely ozonized water 14, is metered for calibrated dosing into the ribbon blender 12 wherein it mixes and reacts with the food ingredients 10. The ozonized water is preferably produced in situ utilizing electrical discharge synthesis.

By way of further explanation, dielectric energy produced between ceramic discs in the presence of water produces ozone dissolved in the water. The ozonized water is unstable and breaks down into water with the release of free radical oxygen. The interaction with the food constituents 10 yields clean inert by-products, namely water and oxygen. The oxygen destroys anaerobic bacteria and viruses in the food constituents 10. It should also be noted that the quantity of water that is added to the food constituents 10 is preadjusted to compensate for the resultant moisture gain upon decomposition of the ozonized water 14.

For the purposes of maximizing the effectiveness of the oxidation treatment within an effective mixing cycle a catalyst 16 is introduced to accelerate the oxidative reaction. The preferred catalyst 16 is a protein derived enzyme, such as available under the trademark Microcatalase, manufactured by Solvay Enzymes, Inc. of Elkhart, Ind. Microcatalase is a standardized liquid enzyme obtained by controlled fermentation of micrococcus lysodeikticus that specifically catalyzes the decomposition of ozonized water into water and molecular oxygen.

The processing sequence further includes mixing the food constituents 10, the ozonized water 14 and the catalyst 16 within the ribbon blender 12 for a fixed period of time usually between five (5) and twenty (20) minutes. In the batch-feed operation as illustrated in FIG. 1, an outfeed door is closed until the food product is thoroughly mixed and the oxidation treatment has been completed.

An oxygen sensor 18 is used for testing the presence of oxygen as a factor of the decomposition of the ozonized water. The sensor 18 transmits signals to a microprocessor 20. The microprocessor 20, in turn, interprets the data and generates a signal to operate a solenoid actuated door release 22 in the blender 12 for discharging the food constituents 10 that have been subjected to the antimicrobial treatment. The microprocessor 20 can optionally transmit data to a chart recorder 24 to provide a print record. The oxygen content can also be detected by titration of the finished food product. The oxygen monitoring sequence using ozonized water however, is not as critical as with hydrogen peroxide for the reason that ozonized water should be found to be generally recognized as safe, by governmental agencies whereas hydrogen peroxide has a limited use status and a governmental requirement for removal of any residue from the finished food product. The microprocessor 20 however, can also be used for generating output signals to control one or more of the ozonized water metering rate, the catalyst introduction rate, the food mixing time and/or the food discharge.

In a continuous-feed system an auger runs constantly and directly into a filing station. This latter modality requires a longer mixing vessel, slower mixing speeds and does not utilize a closed discharge mechanism. The speed and time of the auger can be modulated by a feedback system or by reaction time estimation.

At the completion of the mixing sequence, the sterilized food constituents 10 are discharged into a hopper 26 and subsequently flowably transported through a pipe network 28 for discharge into a plurality of individual containers 30 that are typically positioned on a conveyer belt.

By way of example, a 5%–12% solution of ozone has been found effective as a bactericide and the ozonized water 14 is added to the food constituents 10 in an amount equivalent to about 2%–7% by weight. The ratio may vary and is dependent upon the microbial load during mixing, packing, the temperature, and the acidity of the food constituents.

The enzyme dosage should be approximately 5%–10% by weight of the ozonized water. The reaction time for the oxidation treatment can be further enhanced by the application of heat when appropriate to the food constituents.

The ozone food treatment process of this invention is intended for use particularly when thermal pasteurization compromises the texture and organoliptic integrity of the food product. Furthermore, the food treatment process as described is compatible for aseptic packaging of fresh foods. Previously fresh food products required heat treatment before it could be aseptically packaged.

It should be seen that there is provided an ozone food treatment process which achieves the various objects of this invention and which is well adapted to meet conditions of practical use.

Since possible variations of the process might be made to the exemplary procedures set forth, it is to be understood that the process shown and described should be interpreted as illustrative and not in a limiting sense.

Having thus described the invention, there is claimed as new and desired to be secured by Letters Patent:

1. An ozone food treatment process including the steps of:

(a) preparing a selected combination of food constituents having a moisture component;

(b) mixing the food constituents within a mixing vessel for a predetermined duration;

(c) adding a metered quantity of ozonized water to the food constituents for oxidatively reacting with the food constituents to sterilize and preserve the food constituents; and (d) discharging the sterilized food constituents from the mixing vessel after completion of the oxidation reaction.

2. An ozone food treatment process as claimed in claim 1 further including the step of:

(e) introducing a catalyst for accelerating the oxidative reaction time.

3. An ozone food treatment process as claimed in claim 1 wherein the ozonized water contains approximately 5%–12% dissolved ozone.

4. An ozone food treatment process as claimed in claim 2 wherein the range of catalyst to ozonized water is approximately 5%–10% by weight.

5. An ozone food treatment process as claimed in claim 1 further including the step of:

(f) reducing the moisture content of the food constituents in correspondence with the ozonized water introduced.

6. An ozone food treatment process as claimed in claim 1 further including the step of:

(f) monitoring the reaction time to maximize the oxidative reaction.

7. An ozone food treatment process as claimed in claim 5 wherein the mixing duration is between five and twenty minutes.

8. An ozone food treatment process as claimed in claim 2 wherein the catalyst is a protein derived enzyme.

9. An ozone food treatment process as claimed in claim 2 further including the step of:

(f) monitoring at least one of the ozonized water metering rate, the catalyst introduction rate, the food constituent mixing rate and the food constituent discharge rate.

10. An ozone food treatment process as claimed in claim 9 wherein a microprocessor controlled feedback loop is utilized for the monitoring.

* * * * *